United States Patent [19]

Cancio et al.

[11] Patent Number: 5,147,346
[45] Date of Patent: Sep. 15, 1992

[54] COEXTRUDED MULTI-LAYER THERMOPLASTIC SHEET MATERIAL HAVING ONE LAYER WITH HIGH MODULUS FOR REPOSITIONING TAPE-TAB FASTENERS THEREON, ABSORBANT ARTICLES AND METHODS

[75] Inventors: Leopoldo V. Cancio; James R. Snyder; Pai-Chuan Wu, all of Cincinnati, Ohio

[73] Assignee: Clopay Corporation, Cincinnati, Ohio

[21] Appl. No.: 393,646

[22] Filed: Aug. 14, 1989

[51] Int. Cl.$^5$ .............................................. A61F 13/15
[52] U.S. Cl. .................................... 604/389; 604/390
[58] Field of Search ................ 428/515; 604/358, 389, 604/390, 372

[56] References Cited

U.S. PATENT DOCUMENTS 3,783,871  1/1974  Sabee .................................. 604/372
4,645,501  2/1984  Teed ................................... 604/390

Primary Examiner—Randall L. Green
Assistant Examiner—R. Clarke
Attorney, Agent, or Firm—Wood, Herron & Evans

[57] ABSTRACT

Novel thermoplastic sheet materials, absorbant articles formed therewith and method of producing such sheet materials are disclosed. The novel thermoplastic sheet materials are soft and pliable having a high modulus, high impact resistance and tear strengths and enhanced tape adhesion. The novel thermoplastic sheet materials are formed directly during a coextrusion process which may thereafter include an embossing step. The novel, coextruded thermoplastic sheet materials comprise a plurality of coextruded layers having high modulus outer layers for permitting pressure-sensitive adhesive tape-tab fasteners to be positioned and repositioned thereon without losing substantial tape adhesion therebetween or tearing the sheet materials following their original attachments. The outer layers are formed with a first thermoplastic polymer, such as a polypropylene, having an effective modulus to resist tearing, yielding and deformation upon detaching tape-tab fasteners therefrom, and further having an effective bonding affinity to maintain tape adhesion after initial attachment. The other layer of the thermoplastic sheet materials is an inner layer(s) being formed with a second thermoplastic polymer, such as a polyethylene, to impart softness or low stiffness and effective impact resistance and tear strengths to the sheet materials. The novel thermoplastic sheet materials of the instant invention are suitable for use with articles which, for example, absorb body fluids, and are especially suitable for use as backsheet films in disposable diapers.

17 Claims, No Drawings ical sheet material comprising a plurality of
COEXTRUDED MULTI-LAYER THERMOPLASTIC SHEET MATERIAL HAVING ONE LAYER WITH HIGH MODULUS FOR REPOSITIONING TAPE-TAB FASTENERS THEREON, ABSORBANT ARTICLES AND METHODS

FIELD OF THE INVENTION

The present invention relates to a soft, coextruded thermoplastic sheet material comprising a plurality of coextruded layers with one layer having a high modulus for permitting adhesive tape-tab fasteners to be positioned and repositioned thereon without tearing the sheet material or losing substantial tape adhesion therebetween following their original attachments. The present invention also relates to methods of producing such coextruded sheet materials and absorbant articles formed therewith.

BACKGROUND

It has become common practice to use disposable diapers with infants and incontinent children and adults. Disposable diapers generally have a rectangular or hour-glass shape and comprise an absorbant back material sandwiched between an outer flexible polyethylene backsheet and an inner polypropylene or polyester nonwoven frontsheet. The outer backsheet typically, but not necessarily, is moisture vapor-pervious, but water-impervious to prevent voided liquid absorbed into the absorbant back material from striking through the diaper and soiling the person's adjacent clothing or bedding. The inner front sheet on the other hand is water-pervious to permit the voided liquid to pass therethrough into the absorbant back material to maintain the person in a dry, comfortable state.

It is also well known and common practice in manufacturing disposable diapers to rely upon pressure-sensitive adhesive tape-tab fasteners as means for fastening the diapers about people. The safety advantages and convenience of tape-tab fasteners, rather than pins, is self evident. Notwithstanding their popularity, to date there are several shortcomings associated with the use of tape-tab fasteners. One major shortcoming lies in the loss of tape adhesion between the tape-tab fasteners and backsheets following their original attachments, especially when the backsheets are formed with a polyethylene polymer. Such loss in tape adhesion during normal use discourages users from wanting to use disposable diapers especially in view of costs associated with their use.

Another major shortcoming lies in the tearing of backsheets when the tape-tab fastener, which have high tacky surfaces to prevent tape adhesion loss between the fasteners and the backsheets, are intentionally detached therefrom following their initial attachments, especially when the backsheets are formed with a polyethylene polymer. This tearing phenomenon discourages users from detaching the tape-tab fasteners from the backsheets once the diapers are assembled.

Yet another major shortcoming lies in the stiffness of backsheets formed with high density polyethylene and polypropylene polymers. It is well known to those versed in this field that low stiffness or softness is especially desirable for imparting satisfactory drape qualities to the backsheets. However, backsheets formed with high density polyethylene and polypropylene polymers, as indicated earlier herein, are typically very stiff and brittle and therefore have been known to split or crack on their own during normal use when the disposable diapers are assembled about people. On the other hand, backsheets formed with polyethylene polymers, while softer or less stiffer than backsheets formed with high density polyethylene and polypropylene polymers, are known to tear when the tape-tab fasteners are intentionally detached therefrom for repositioning.

These shortcomings become immediately apparent when users, such as parents, attempt to use disposable diapers formed with these backsheets, and more particularly attempt to unfasten the tape-tab fasteners to routinely inspect for soiled diapers and then refasten same following inspection. Consequently, these inefficiencies in the backsheets have resulted in unsoiled, disposable diapers being commonly discarded during normal use and following routine inspection, especially during the toilet-training ritual. The lack of reuseability of disposable diapers due to the shortcomings associated with the backsheets available heretofore is not only inconvenient but is also expensive in view of rising costs associated with disposable diapers.

In an attempt to resolve these problems with conventional polyethylene and polypropylene back-sheets, the disposable diaper manufacturers have resorted to gluing strips of heavy gauge, typically 2-3 mils, polypropylene onto conventional low density polyethylene backsheets to form heterologous backsheets having distinct, stiff landing or positioning zones for receiving the tape-tab fasteners thereon. Unfortunately, this is a costly procedure, since it requires the use of adhesives to affix the polypropylene strips thereto and additional processing steps to formulate these heterologous backsheets.

Consequently, there is a present need for backsheets for use with absorbant articles, such as disposable diapers, which are soft and pliable, but which do not tear upon detaching the tape-tab fasteners from such backsheets for repositioning or lose substantial tape adhesion therebetween during normal use following original attachment, and which do not require additional materials and non-extruding processing steps to form same.

SUMMARY OF THE INVENTION

In brief, the present invention alleviates the above-mentioned problems and shortcomings of the present state of the art through the discovery of a novel, coextruded sheet material for use with articles which use adhesive tape-tab fasteners therewith, such as articles that absorb body fluids. More particularly, a novel, coextruded sheet material of the present invention is uniquely designed with an outer layer especially adapted for positioning and repositioning adhesive tape-tab fasteners thereon so that when the tape-tab fasteners are intentionally detached therefrom following original attachment for repositioning, this is done so without tearing the coextruded sheet material and without experiencing substantial loss in tape adhesion following reattachment.

A novel, coextruded thermoplastic sheet material of the present invention comprises a plurality of coextruded layers wherein at least one layer is an outer layer and the other layer is an inner layer. The coextruded outer-layer is formed with a first thermoplastic polymer having a high bonding affinity for the adhesive utilized with the tape-tab fasteners to maintain the tape adhesion therebetween when the tape-tab fasteners are positioned thereon, and further having a high modulus which will resist deforming, yielding and/or tearing upon detaching the tape-tab fasteners for repositioning. The coextruded inner layer on the other hand is formed with a second thermoplastic polymer having a bonding affinity for the adhesive which typically is somewhat less than that of the first thermoplastic polymer, but which imparts to the sheet material softness or low stiffness and effective impact resistance and tear strength.

Thus, it has been discovered that when the teachings of the present invention are followed, a surprisingly novel, coextruded sheet material is produced which is soft and pliable having good drape qualities, but which has effective bonding affinity, impact resistance and tear strength so that adhesive tape-tab fasteners utilized therewith can be positioned and repositioned on the outer layer of the sheet material without tearing the sheet material or experiencing substantial loss in tape adhesion therebetween following their original attachments.

The first thermoplastic polymer can be, for instance, a polypropylene, a polypropylene copolymer, a polyester such as a polyethylene terephthalate (PET) and a polyester copolymer of terephthalic acid, ethylene glycol and cyclohexane dimethanol (PETG) an alphamethyl styrene and styrenic copolymers. The second thermoplastic polymer can be, for instance, a polyethylene, an ethylene or propylene copolymer, an ethylene vinyl acetate copolymer, and an ethylene methyl acrylate copolymer.

The unique softness and effective impact and tear strengths and tape adhesion associated with the coextruded thermoplastic sheet materials of the present invention are accomplished without adversely affecting the properties or cost of the sheet materials while obtaining the desired advantages of permitting repositionable use of tape-tab fasteners therewith. Accordingly, when following the teachings of the present invention, manufacturers of absorbant articles, such as disposable diapers, are no longer required to glue strips of polypropylene material or the like onto conventional backsheets to form distinct, rigid landing zones for receiving the tape-tab fasteners thereon, since the coextruded thermoplastic sheet materials of the instant invention can be formulated for compatible use with almost any pressure-sensitive adhesive tape-tab fastener commercially available or otherwise.

The novel, coextruded thermoplastic sheet materials of this invention are especially suitable for use as films which can be used as backsheets to form novel absorbant articles, such as bandages, surgical dressings or drapes and catamenial pads, and are especially suitable for use as backsheets to form novel disposable diapers. When the novel, coextruded thermoplastic sheet materials of this invention are used as backsheets to form novel disposable diapers, they uniquely afford cost saving and convenient advantages to users by permitting them to position and reposition tape-tab fasteners on the backsheets with confidence following routine inspection during, for instance, the toilet-training ritual so that unsoiled disposable diapers can be reused. In other words, the refastened tape-tabs will adhere firmly to the novel backsheets, and the disposable diapers will remain in place without deforming, yielding or tearing during normal use, especially following their opening or removal by users. Moreover, since the novel backsheets have good drape qualities and are uniquely soft with effective impact resistance and tear strength, they will not split or crack on their own during use, nor will they tear when users attempt to detach the tape-tab fasteners from the backsheets following initial assembly of the disposable diapers.

The present invention therefore now makes it possible to close a disposable diaper with confidence and to open the originally closed diaper for occasional inspection without fear that the tape-tab fasteners will tear the backsheets or will not reposition on the backsheets following the original assembly or subsequent assemblies of unsoiled disposable diapers. It should therefore be apparent to those versed in this field that the problems attendant with previous conventional backsheets are overcome in a relatively simple yet unobvious manner by the present invention.

The above features and advantages will be better understood with reference to the detailed description and examples. It also should be understood that the particular coextruded thermoplastic sheet materials and absorbant articles of this invention are exemplary only and not to be regarded as limitations of the invention.

DETAILED DESCRIPTION OF THE INVENTION

By way of illustrating and providing a more complete appreciation of the present invention and many of the attendant advantages thereof, the following detailed description and examples are given concerning the novel, coextruded thermoplastic sheet materials, absorbant articles made therewith and methods of making same.

As used herein, the term "tape adhesion" or "tape peel strength" refers broadly to the force required to remove or separate an adhesive fastener such as a pressure-sensitive adhesive fastener from a thermoplastic sheet material. The force required to remove or separate the fastener from the thermoplastic sheet material is generally measured at a specific angle and at a given speed. Tests to determine tape adhesion may be conducted with an one-inch width fastener, such as a pressure-sensitive adhesive fastener, at 90°, 120° and 180° angles of peel at a pull speed of approximately 12 inches per minute or at any other desired speed. The results may be expressed in grams per inch width of the tape-tab fastener.

Referring now more particularly to the present invention, novel thermoplastic sheet materials for use with articles which absorb, for instance, body fluids are formed directly during an extrusion process which may thereafter include an embossing step. This is accomplished by coextruding a composite film having at least two layers wherein one layer is an outer layer formed with a first thermoplastic polymer and the other layer is an inner layer formed with a second thermoplastic polymer to form the composite film which has good drape qualities and which permits pressuresensitive adhesive tape-tab fasteners to be positioned and repositioned thereon without experiencing substantial loss in tape adhesion therebetween or tearing the film following their original attachments. A preferred thickness of the outer layer of a composite film is from between about 0.4 mils to about 1.0 mils, especially when it is formed with a polypropylene and the inner film layer is formed with a polyethylene. A preferred thickness of a composite film is from between about 0.8 mils to about 2.0 mils and more preferably from between about 1.0 mils to about 1.5 mils. It should of course be understood that the overall thickness of a composite film of the present invention and the ultimate thickness of each coextruded layer depends upon the characteristics of each thermoplastic polymer selected to formulate each coextruded layer and the overall properties desired to be imparted to each composite film produced, as more fully developed hereinafter.

Coextrusion techniques are well known to those versed in the art and need not be discussed in detail. One such technique for coextruding films includes the use of a feed block located between separate extruders and a die. The feed block serves to combine various thermoplastic resin streams flowing from the separate extruders into intimate contact with one another to form a single stream and to direct the combined streams in a parallel flow pattern into the die for formation of the coextruded composite film. In the event that varying widths are desired with respect to each layer of the composite film and especially the outer layer, converging dies, each having a different width, can be employed to combine the thermoplastic streams flowing out from the separate extruders into intimate and overlapping contact with one another. With this method, however, the feed block is eliminated, and for each extruder employed, a corresponding die is utilized for receiving the thermoplastic stream flowing out therefrom. It should of course be understood that when the composite film is coextruded with the outer layer having a narrower width, the die corresponding to the outer layer will have a width which is less than that of the die corresponding to the inner layer. See Example IV discussed hereinafter.

Like coextrusion techniques, embossing techniques are well established and need not be discussed in detail. Exemplary of techniques that may be employed include extruding the composite films between a chill metal embossing roll and a rubber roll located downstream from the die for receiving the combined thermoplastic streams flowing therefrom or embossing the formed composite films under heat and pressure with a roll having a selected surface pattern. The outer layers of the composite films of the present invention may have male or female embossed surfaces depending of course upon which sides of the films are in contact with the embossing rolls.

The thermoplastic polymers selected to form the layers of the composite films of the present invention are not critical so long as, at the thicknesses employed, they impart properties not inconsistent with the teachings of this invention. For example, the preferred use of the composite films of the present invention are as the outer liquid-impervious layers for absorbant articles, such as disposable diapers and the like. For these purposes, softness or low stiffness, yet enhanced bonding affinity and high impact resistance and high tear strengths are essential. To accomplish same, the outer layer of a composite film should therefore be formed with a thermoplastic polymer which has a high or effective modulus and bonding affinity for the pressure-sensitive adhesive. The bonding affinity, however, should not be so high that it exceeds the tear strength of the film. The modulus on the other hand should be high enough so that at the thickness employed, the tape-tab fasteners can be positioned and repositioned thereon following original attachment without tearing the film. With respect to the inner layer of a composite film, it should be formed with a thermoplastic polymer which imparts to the composite film a degree of softness or low stiffness and high or effective impact resistance and tear strength to offset the stiffness, brittleness and enhanced tape adhesion imparted to the composite film via the thermoplastic polymer selected to formulate the outer layer.

It should therefore be understood that the unique features of the composite films of the present invention are dictated by both the thicknesses of and the thermoplastic polymers selected to formulate each layer. For instance, repositionability of a pressure-sensitive adhesive tape-tab fastener on a composite film of the present invention when used as a backsheet in a disposable diaper depends on the tape-tab fastener employed and the CD tensile strength at low elongation (below about 25% elongation) of such backsheet. The CD tensile strength at low elongation of such a composite film may be adjusted, for example, by the thickness of the high modulus or outer layer as well as the density of the inner or polyethylene layer, as more fully illustrated in the examples to follow. Moreover, the tape peel strength may also be controlled by embossing. Nevertheless, it should be appreciated that such adjustments should be made in conjunction with the particular tape-tab fasteners selected for use therewith in order to accomplish the objectives of the present invention.

As already indicated herein, it is important that the composite films of the present invention are formulated in such a manner that they are soft or have low stiffness. Such softness or low stiffness is desirable for imparting satisfactory drape qualities and effective impact and tear strengths to the composite films, especially when they are utilized as backsheets in disposable diapers. The softness or stiffness as measured by the secant modulus at about 1% elongation of the overall composite films should therefore be in the range of from between about 20,000 psi to about 80,000 psi and preferably from between about 30,000 psi to 50,000 psi. While the overall softness or stiffness of the composite films is dictated by all layers, the inner layers are preferably formed with thermoplastic polymers which impart softness and low stiffness to the composite films whereas the outer layers are formed with thermoplastic polymers with effective modulus which impart enhanced tape adhesion between the composite films and the pressure-sensitive adhesives utilized with tape-tab fasteners.

Examples of suitable thermoplastic polymers that can be used to form the outer layer include a polypropylene, a high density polyethylene, a polypropylene copolymer such as an ethylene-propylene copolymer, a styrene polymer, a styrenic copolymer such as alpha-methyl styrene, and a polyester such as a polyethylene terephthalate (PET) and a polyethylene terephthalate glycol copolymer (PETG). Examples of suitable thermoplastic polymer materials that can be used to form the inner layer(s) include ultra low, low or medium density polyethylene, low, medium, high or ultra-high molecular weight polyethylene, polypropylene copolymers, ethylene copolymers, and ethylene copolymers with vinyl acetate or methyl acrylate.

A preferred thermoplastic polymer for the outer layer of the present invention is a polypropylene having a density of from between about 0.89 grams/cc to about 0.91 grams/cc. A preferred thermoplastic polymer for the inner layer of the present invention is a low or medium density polyethylene, i.e., a density from between about 0.910 g/cc to about 0.951 g/cc. Suitable sources for the polyethylene include Eastman Chemical Co., Dow Chemical Co., Union Carbide, Mobile Chemical Co. and Quantum Chemical Co., whereas suitable sources for the polypropylene include Eastman Chemical Co., Quantum Chemical Co., Aristech Chemical Co., El Paso Co., Hercules Corp. and Himont Co.

One or more layers of a composite film of the instant invention may be pigmented to impart desirable aesthetic qualities such as by employing a colored or white pigment therein, such as titanium dioxide. Desirably, the pigmented layer is the non-outer layer in a two layered composite film or the intermediate and/or non-outer (inner) layer(s) in a three or more layered composite film construction. In addition to being pigmented, one or more of the thermoplastic resin layers can employ conventional additives, such as slip additives, antioxidants, plasticizers, fillers and so forth. These would be employed in their normal amounts well known to those versed in this field.

In producing the composite films of the present invention by the coextrusion techniques, the outer layer may be formed with any width compatible with the teachings of the present invention. For example, a composite film may be formed with an outer layer having a width equal to or less than that of the other layer(s). Thus, in the event that a composite film of the instant invention formed with outer and inner layers is selected for use as a backsheet in a disposable diaper, and the backsheet is formed with a longitudinal width of from between about 16 to about 20 inches and a lateral width of from between about 10 to about 14 inches, the outer layer may be formed with a lateral width equal to that of the inner layer and a longitudinal width of approximately 1 to 4 inches or more and strategically located in an area on the backsheet for creating a landing zone for positioning the adhesive tape-tab fasteners thereon when the disposable diaper is in an assembled form. See Example IV discussed hereinafter.

The thermoplastic sheet materials of the present invention are especially suitable for use with absorbent articles, such as disposable diapers, bandages, surgical dressings or drapes and catamenial pads and most particularly with disposable diapers. When the thermoplastic sheet materials are to be used with absorbent articles, they can be formulated into thin films that are either liquid-pervious or liquid-impervious, that have either smooth or embossed surfaces and that have either dull or glossy finishes. The thickness of the film can vary over a wide range. When the thermoplastic sheet materials are to be formulated into thin films that are to be used as backsheets for absorbent articles, it is preferred, but not necessary, that the thin films are moisture-impervious having embossed surfaces and dull finishes. Typically, such thin backsheet films can have a thickness ranging from between about 0.8 mils to about 2.0 mils and preferably from between about 1.0 mils to about 1.5 mils, but these limitations are not critical. Of course, when selecting a film thickness, the repositionability of tape-tab fasteners and the tearing strength of a composite film should not be overlooked so that the objectives of the present invention are not defeated.

A typical disposable diaper practicing the objectives of the present invention generally includes a moisture-pervious inner front sheet, an outer backsheet of the present invention which is preferably moisture-impervious, and absorbent material or layer positioned between the outer backsheet and inner front sheet and tape-tab fasteners secured to the disposable diaper. The moisture-pervious inner front sheet forms the diaper inside surface for direction toward a person and the outer backsheet forms a diaper outside surface for direction away from the person when the disposable diaper is worn by the person. To secure the tape-tab fastener to the disposable diaper, the tape-tab fasteners generally speaking have anchoring ends which are secured to the disposable diaper and user ends which have on one side thereof a pressure-sensitive adhesive presenting tacky surfaces facing in the same direction as the diaper inside surface for contact with the backsheet when the diaper is fitted about the person. Other absorbent articles such as bandages, surgical dressings or drapes and catamenial pads, on the other hand, generally comprise the same three elements as the disposable diaper absent the tape-tab fasteners.

Examples of composite films of the present invention will now be further illustrated with reference to the following examples.

EXAMPLE I

Four two-layered composite films of the present invention are coextruded with an apparatus having two individual extruders which feed into a feed block having two passageways which ultimately feed into a die. One extruder having a 2¼inch screw feeds molten low density polyethylene obtained from, for example, Dow Chemical Co., Union Carbide, Mobile Chemical Co., etc., into one passageway of the feed block, and a 2½ inch extruder feeds molten polypropylene obtained from, for instance, Eastman Chemicals Co., Aristech Chemical Co. and the like, into the other passageway. The resins are coextruded from the die as composite films. The thicknesses of the outer polypropylene layers of the four composite films that are produced vary from about 0.4 mils to about 0.6 mils. The coextruded composite films have a thickness of about 1.2 mils. Table I sets forth the three films.

TABLE I

|  | Composite Film I | Composite Film II | Composite Film III |
|---|---|---|---|
| PP outer layer* thickness (mil) | 0.4 | 0.6 | 0.4 |
| PE other layer** thickness (mil) | 0.8 | 0.6 | 0.8 |
| PE density (g/cc) | 0.922 | 0.922 | 0.939 |
| CD tensile strength*** at 25% elongation 20"/min crosshead speed (g/in) | 840 | 945 | 1170 |
| CD tensile strength at 10% elongation 5"/min crosshead speed (g/in) | 710 | 780 | 965 |

*PP = polypropylene.
**PE = Polyethylene. Various polyethylenes may be blended to adjust the density.
***Repositionability of a tape-tab fastener on a backsheet of a disposable diaper depends upon the tape-tab fastener and the cross directional (CD) modulus of the backsheet film used. CD modulus can be adjusted by thickness of the PP layer as well as the density of PE layer.

As can be seen from Table I, the CD tensile strength at about 25% elongation which is measured at about 20 inches per minute crosshead speed while stretching and CD tensile strength at about 10% elongation at about 5 inches per minute crosshead speed while stretching varies between the composite films.

EXAMPLE II

The tape adhesion as measured in grams is compared between composite films I and III of the present invention referenced in Example I and two distinct disposable diapers having landing zones glued onto the backsheets. The results are tabulated in Tables II and III as follows.

TABLE II

| Tape Adhesion Measurement (grams) | First Disposable Diaper Having a Landing Zone Thereon Tape-tab on Landing Zone* | Composite Film I PP/PE Coextrusion Tape-tab on PP Surface* | Composite Film III PP/PE Coextrusion Tape-tab on PP Surface* |
| --- | --- | --- | --- |
| 90° peel force | 510 | 620 | 810 |
| 180° peel force | 700 | 1170 | 1370 |
| 120° peel force | 580 | 740 | 790 |

*Tape-tabs used are type supplied with the first disposable diaper, and the width of the tabs is one inch.

TABLE III

| Tape Adhesion Measurement (grams) | Second Disposable Diaper Having a Landing Zone Thereon Tape-tab on Landing Zone* | Composite Film I PP/PE Coextrusion Tape-tab on PP Surface* |
| --- | --- | --- |
| 90° peel force | 120 | 620 |
| 180° peel force | 150 | 1170 |
| 120° peel force | 390 | 740 |

*Tape-tabs used are type supplied with the second disposable diaper, and the width of the tabs is one inch.

As can be seen in Tables II and III, the tape adhesion, as measured in grams at 90°, 180° and 120° peel forces, is greater for both composite films I and III then for either of the two disposable diapers having landing zones glued thereon.

EXAMPLE III

The tape adhesion, as measured in grams at 90°, 180° and 120° peel forces, is compared between composite films I and IV of the present invention referenced in Example I and the first disposable diaper having a landing zone glued onto the backsheet. The results are tabulated as follows in Table IV.

TABLE IV

| | PP/PE Coextruded During this Invention | | |
| --- | --- | --- | --- |
| Tape Adhesion Measurement (grams) | First Disposable Diaper Having a Landing Zone Thereon Tape-tab on Landing Zone* | Composite Film I Surface (female, pin down) 250 lines/in Tape-tab on PP Surface* | Composite Film IV** Surface (Male, pin up) 250 lines/in Tape-tab on PP Surface* |
| 90° peel (grams) | 510 | 620 | 1330 |
| 180° peel (grams) | 700 | 1170 | 2100 |
| 120° peel (grams) | 580 | 740 | 900 |

*Tape-tabs used are type supplied with the first disposable diaper, and the width of the tabs is one inch.
**The formulation of composite film IV is identical to the formulation of composite film III tabulated in Table I herein.

With respect to Table IV, the composite films I and IV are formed with embossed female (250 lines/inches) and male (250 lines/inches) surfaces, respectively. The tape adhesion, as measured in grams at 90°, 180° and 120° peel forces, is greater for both embossed, composite films I and IV than the first disposable diaper having a landing zone glued thereon. The tape peel force can be controlled as is demonstrated in Table IV through various embossing patterns.

EXAMPLE IV

In the event that a coextruded composite film of the instant invention, i.e., a coextruded composite film formed with an outer layer having a narrower width than the inner layer, is selected for use as backsheets in disposable diapers, the backsheets may be produced from such a coextruded composite film in accordance with the following exemplary technique. In the production of backsheets in general, it goes without saying that they should be sized to correspond to the dimensions of the disposable diapers with which they will be used. Disposable diapers generally speaking are rectangular in shape and are about 16"-20" and typically 18" in length (longitudinally), i.e., top-to-bottom, and about 10"-14" and typically 12" in width (laterally), i.e., side-to-side. With this in mind, this exemplary technique will be described in reference to the formation of coextruded backsheets, each being generally sized at 18"×12" and having outer and inner layers wherein the outer layers have widths narrower than the inner layers. More particularly, each such backsheet is formed with one inner layer sized at 18"×12" and two separate outer layers, each being sized at 2"×12" and located on the same side of the inner layer, but oppositely opposed and adjacent the top and bottom 12" lateral edges, respectively. In this exemplary method of production, the outer layers are formed with polypropylene and the inner layer is formed with polyethylene.

In accordance with this technique, a coextruded composite film is first produced in bulk which is then subjected to at least three separate-type cuts to ultimately form the coextruded 18"×12" backsheets. The equipment includes five separate extruders of various sizes corresponding to five separate dies. Since in this example, the bulk coextruded composite film that is initially produced has a lateral width, i.e., side-to-side, of 66", one such die also has a width of 66". The 66" die is used to form the inner polyethylene layer. The other four dies, each having widths of 4", are used to form the outer polypropylene layers. It should of course be understood by those versed in this art that the size or widths and placement of the dies selected to coextrude the bulk composite film are of course dependent upon the dimensions of the layers of the coextruded backsheets and the number of layers being produced. Moreover, it should be understood by those skilled in this field that any dies having suitable widths for forming the inner and outer layers which accomplishes such objectives may be selected.

In this example, since 18"×12" backsheets having two separate 2"×12" outer polypropylene layers, each being located on the same side of the inner polyethylene layer and across the top and bottom lateral edges thereof, respectively, are being produced, all four 4" dies should be located either above or below the 66" die and each should be strategically spaced apart, i.e., 18", to selectively form the outer polypropylene layers. More particularly, the first 4" die is located 4" from one side edge of the 66" die and the remaining dies are selectively and serially spaced 18" apart from one another and therefrom. With the 66" and 4" dies arranged in this formation, a coextruded composite film will be produced in bulk which is typically 500' or more in length. Following the coextrusion step, the bulk coextruded composite film that is produced can be characterized as follows. The bulk film consists of a inner polyethylene layer having a lateral width of 66" and a longitudinal width of 500' or more, and four outer polypropylene layers having lateral widths of 4" and longitudinal widths of 500' or more. The four outer polypropylene layers are spaced 18" apart from one another. It should be appreciated that each outer polypropylene layer, which is located adjacent each longitudinal side edge of the 66" inner polyethylene layer, is preferably located approximately 4" from such longitudinal side edge.

In processing the bulk coextruded composite film, 6" is first trimmed from each longitudinal side edge of the bulk film to remove the edge beas, i.e., the swollen and non-uniform portions of the film. In so doing, a 6" longitudinal strip of the inner polyethylene layer and a 2" longitudinal strip of the outer polypropylene layer are removed from each longitudinal side edge of the 66" bulk film to generate a bulk film having a net width of 54". This represents the first-type cut. The 54" width bulk film is then sliced longitudinally at 18" widths to generate three bulk 18" lateral width film strips. Each 18" lateral width film strip has an inner polyethylene layer having a lateral width of 18" and a longitudinal width 500' or more and two outer polypropylene layers, each having a lateral width of 2" and a longitudinal width of 500' or more. The two 2" lateral width outer polypropylene layers are spaced 14" apart and located adjacent the longitudinal side edges of the 18" lateral width film strips. This represents the second-type cut. As indicated already, these 18" lateral width film strips are approximately 500' or more in length and may be wound into separate rolls for storage or shipment.

To ultimately produce the coextruded 18"×12" backsheets, however, each 18" lateral width film strip is further sliced, but at a 90° angle at 12" intervals to generate the 18"×12" coextruded backsheets. This represents the third-type cut. To characterize the selectively coextruded 18"×12" backsheets, they each have an 18"×12" inner polyethylene layer and two separate 2"×12" outer polypropylene layers, one outer polypropylene layer being located adjacent and laterally along the top edge of the inner polyethylene layer and the other outer polypropylene layer being located adjacent and laterally along the bottom edge of the inner polyethylene layer. It should be appreciated by those skilled in this art that the 2"×12" outer polypropylene layer located along the lateral top edge of the inner polyethylene layer forms a distinct, yet integral landing zone on which tape-tab fasteners can be positioned and repositioned when the disposable diaper is in an assembled form. It should also be appreciated by those versed in this field that the 2"×12" outer polypropylene layer located along the lateral bottom edge of the inner polyethylene layer provides balance to the 18" lateral width film strip, especially with respect to the thickness of the bulk composite 18" lateral width film strip along the longitudinal side edges thereof, so that prior to the final processing 90° cuts, the bulk 18" lateral width film strips can be conveniently wound into somewhat tight and even rolls for storage or shipment. It of course should further be appreciated that it is not necessary to provide the outer polypropylene layer strip along the lateral bottom edges of the backsheets to still meet the objectives of the instant invention. In that event, the width and spacing of the dies selected to form the bulk coextruded composite film should be arranged accordingly.

The present invention may therefore, of course, be carried out in other specific ways than those herein set forth without departing from the spirit and essential characteristics of the present invention. As indicated earlier, the width of the outer layer of a composite film of the present invention may be equal to or less than the width of the other inner layers of the composite film. Moreover, the composite films of the instant invention may be formed with one or more outer layers having identical but such widths being narrower than the widths of the inner layers or varying widths. The present embodiments are, therefore, to be considered in all respects as illustrative and not restrictive and any changes coming within the meaning and equivalency range of the appended claims are to be embraced therein.

Having described our invention, we claim:

1. A coextruded thermoplastic sheet material having an outer layer especially adapted for positioning and repositioning adhesive tape-tab fasteners thereon, said sheet material having an overall thickness of from between about 0.5 mils to about 2.0 mils and an overall stiffness of from between about 20,000 psi to about 80,000 psi as measured by secant modulus at about 1% elongation and comprising at least two coextruded layers, a first layer being said outer tape-tab fastener securing layer formed with a first thermoplastic polymer having an effective modulus for resisting tear when detaching the adhesive tape-tab fasteners therefrom and an effective bonding affinity for maintaining between said outer layer and the adhesive tape-tab fasteners, and a second layer being an inner layer formed with a second thermoplastic polymer for imparting softness and effective impact strength to said sheet material, said outer layer forming a landing zone for positioning and repositioning tape-tab fasteners thereon, so that when the tape-tab fasteners are initially positioned on said outer layer and intentionally detached therefrom for repositioning thereon, said sheet material neither tears nor loses substantial adhesion therebetween.

2. A coextruded thermoplastic sheet material of claim 1, said sheet material having an overall thickness of from between about 1.0 mils and about 1.5 mils and said outer layer having a thickness of from between about 0.4 mils and about 1.0 mils.

3. A coextruded thermoplastic sheet material of claim 1, said first thermoplastic polymer being a polypropylene and said second thermoplastic polymer being a polyethylene.

4. A coextruded thermoplastic sheet material of claim 1, said second thermoplastic polymer being a polyethylene.

5. A coextruded thermoplastic sheet material of claim 1, said second thermoplastic polymer being a polyethylene having a density of from between about 0.910 grams/cc to about 0.951 grams/cc.

6. A coextruded thermoplastic sheet material of claim 1, said first thermoplastic polymer being a polypropylene having a density of from between about 0.89 grams/cc to about 0.91 grams/cc.

7. A coextruded thermoplastic sheet material of claim 1, said sheet material having an overall stiffness of from between about 30,000 psi to about 50,000 psi as measured by secant modulus at about 1% elongation.

8. A coextruded thermoplastic sheet material of claim 1, said first thermoplastic polymer being selected from the group consisting of a high density polyethylene, a polyester, a polypropylene copolymer, a styrene polymer and a styrenic copolymer.

9. A coextruded thermoplastic sheet material of claim 1, said second thermoplastic polymer being selected from the group consisting of an ethylene vinyl acetate copolymer, an ethylene methyl acrylate copolymer, an ultra low, low and medium density polyethylene, a polypropylene copolymer and a polyethylene copolymer.

10. A coextruded thermoplastic sheet material of claim 1, said sheet material being a backsheet in a disposable diaper which forms a diaper outside surface for direction away from a person when the disposable diaper is worn by the person.

11. A coextruded thermoplastic sheet material of claim 1 wherein the width of said outer tape-tab fastener layer is less than the width of said inner layer.

12. A coextruded thermoplastic sheet material of claim 1, said sheet material being a backsheet in an article that absorbs body fluids wherein the article is selected from the group consisting of a catamenial pad, surgical drape and bandage.

13. A disposable diaper having an improved backsheet for positioning and repositioning adhesive tape-tab fasteners thereon without tearing the backsheet or losing substantial tape adhesion therebetween following initial attachments of the adhesive tape-tab fasteners to the backsheet, said disposable diaper comprises:

a liquid-pervious front sheet which forms a diaper inside surface for direction toward a person when the disposable diaper is worn by the person;

an adhesive tape-tab fastener having an anchoring end and an user end, the anchoring end being secured to said disposable diaper and the user end having on one side thereof a pressure-sensitive adhesive presenting a tacky surface facing in the same direction as the diaper inside surface;

said backsheet which forms a diaper outside surface for direction away from the person when the disposable diaper is worn by the person, said backsheet being a coextruded plastic film having an overall thickness of from between about 0.8 mils to about 2.0 mils and an overall stiffness of from between about 20,000 psi to about 80,000 psi as measured by secant modulus at about 1% elongation and comprising at least two coextruded layers, one said layer being an outer layer which forms a landing zone for positioning and repositioning said adhesive tape-tab fastener thereon and being formed with a thermoplastic polymer having an effective modulus for resisting tear when detaching said adhesive tape-tab fastener therefrom and an effective bonding affinity for maintaining tape adhesion, said other layer being an inner layer formed with a thermoplastic polymer for imparting softness and effective impact strength to said backsheet, so that when the tacky surface of the user end of said adhesive tape-tab fastener is initially positioned on said outer layer via the pressure-sensitive adhesive and intentionally detached therefrom for repositioning thereon, said backsheet does not tear or lose substantial tape adhesion between said outer layer and said adhesive tape-tab fastener; and an absorbent material located between said front sheet and said backsheet.

14. A disposable diaper of claim 13, said backsheet having an overall stiffness of from between about 30,000 psi and 50,000 psi as measured by secant modulus at about 1% elongation.

15. A disposable diaper of claim 13, a width of said outer layer being less than the width of said inner layer and said outer layer being selectively located on said backsheet for creating a landing zone for said adhesive tape-tab fastener to be positioned and repositioned thereon when said disposable diaper is in an assembled configuration.

16. A disposable diaper of claim 15 said inner layer having a longitudinal width of from between about 16 to about 20 inches and a lateral width of from between about 10 to about 14 inches and said outer layer having a longitudinal width of from between about 1 to about 4 inches and a lateral width which is about equal to that of said inner layer.

17. A disposable diaper of claim 13 said backsheet having an overall thickness from between about 1 0 mils to about 1.5 mils, said outer layer having a thickness of from between about 0.4 mils and 1.0 mils and being formed with a polypropylene polymer having a density of from between about 0.89 grams/cc to about 0.91 grams/cc, and said inner layer being formed with a polyethylene polymer having a density of from between about 0.910 grams/cc to about 0.951 grams/cc.

* * * * *